(12) United States Patent
Yoshida et al.

(10) Patent No.: US 11,801,026 B2
(45) Date of Patent: Oct. 31, 2023

(54) RADIOGRAPHIC IMAGING APPARATUS

(71) Applicant: Shimadzu Corporation, Kyoto (JP)

(72) Inventors: Takanori Yoshida, Kyoto (JP); Fumiaki Tanaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 383 days.

(21) Appl. No.: 16/679,790

(22) Filed: Nov. 11, 2019

(65) Prior Publication Data

US 2020/0146755 A1    May 14, 2020

(30) Foreign Application Priority Data

Nov. 13, 2018 (JP) .................. 2018-213204

(51) Int. Cl.
| | |
|---|---|
| G06T 7/246 | (2017.01) |
| A61B 6/00 | (2006.01) |
| A61B 34/20 | (2016.01) |
| G06T 7/73 | (2017.01) |
| G06T 7/00 | (2017.01) |
| A61B 90/00 | (2016.01) |
| A61M 25/10 | (2013.01) |

(52) U.S. Cl.
CPC ............ *A61B 6/5217* (2013.01); *A61B 34/20* (2016.02); *A61B 90/37* (2016.02); *A61M 25/104* (2013.01); *G06T 7/0016* (2013.01); *G06T 7/246* (2017.01); *G06T 7/73* (2017.01); *A61B 2034/2065* (2016.02); *A61B 2090/376* (2016.02); *A61M 2025/1079* (2013.01); *G06T 2207/10116* (2013.01); *G06T 2207/30021* (2013.01); *G06T 2207/30101* (2013.01); *G06V 2201/034* (2022.01)

(58) Field of Classification Search
None
See application file for complete search history.

(56) References Cited

U.S. PATENT DOCUMENTS

| | | | |
|---|---|---|---|
| 2005/0002546 A1* | 1/2005 | Florent | ............... G06T 5/50 382/128 |
| 2006/0004286 A1* | 1/2006 | Chang | ............... A61B 90/16 606/198 |

(Continued)

FOREIGN PATENT DOCUMENTS

| | | |
|---|---|---|
| CN | 108140238 A | 6/2018 |
| JP | H07-079955 A | 3/1995 |

(Continued)

OTHER PUBLICATIONS

First Office Action dated Feb. 18, 2023 issued in relation to the corresponding Chinese Patent Application No. 201911106011.7 together with an English-language machine translation thereof.

(Continued)

*Primary Examiner* — Patricia J Park
(74) *Attorney, Agent, or Firm* — Muir Patent Law, PLLC (57) ABSTRACT

A radiographic imaging apparatus includes an image processor configured to perform image processing on a radiation image generated by an image generator, and a display configured to display a processed image that has been subjected to the image processing in the image processor. The image processor is configured to perform control to create the processed image showing an expanded portion in which a balloon introduced into a subject is expanded.

15 Claims, 8 Drawing Sheets

(56) References Cited

U.S. PATENT DOCUMENTS

| | | | | |
|---|---|---|---|---|
| 2006/0116586 A1* | 6/2006 | Sekiguchi | ................ | A61B 1/01 |
| | | | | 600/470 |
| 2008/0045827 A1* | 2/2008 | Rongen | ................ | A61B 6/504 |
| | | | | 600/407 |
| 2010/0172556 A1* | 7/2010 | Cohen | ................ | A61B 18/1492 |
| | | | | 600/407 |
| 2011/0160661 A1* | 6/2011 | Elton | ................ | A61M 25/10 |
| | | | | 604/103.06 |
| 2011/0170662 A1* | 7/2011 | Baumgart | ................ | A61B 6/504 |
| | | | | 378/62 |
| 2011/0238082 A1* | 9/2011 | Wenderow | ........ | A61M 25/0105 |
| | | | | 606/130 |
| 2015/0141807 A1* | 5/2015 | Fetterly | ................ | A61B 6/12 |
| | | | | 600/424 |

FOREIGN PATENT DOCUMENTS

| | | | |
|---|---|---|---|
| JP | 2009-297457 A | 12/2009 |
| JP | 5337525 B2 | 11/2013 |
| JP | 2018-525082 A | 9/2018 |
| JP | 2018-526144 A | 9/2018 |

OTHER PUBLICATIONS

Notice of Reasons for Refusal dated Feb. 1, 2022 for corresponding Japanese Patent Application No. JP2018-213204, submitted with a machine translation.

* cited by examiner

X-RAY IMAGE                REGION OF INTEREST

FIG.5

REFERENCE IMAGE

FIG.6

DEGREE OF SIMILARITY
TO REFERENCE IMAGE

PERIOD OF BALLOON EXPANSION AND
RECOGNITION OF BALLOON EXPANSION

FIG.7A

PRIOR TO BALLOON EXPANSION

FIG.7B

EARLY STAGE OF BALLOON EXPANSION

FIG.7C

MAXIMUM BALLOON EXPANSION

FIG.7D

LATE STAGE OF BALLOON EXPANSION

FIG.7E

END OF BALLOON EXPANSION

FIG.8

EXPANSION RECOGNITION IMAGE        X-RAY IMAGE

FIG.9

EXPANSION RECOGNITION IMAGE                    X-RAY IMAGE

FIG.10

EXPANSION RECOGNITION IMAGE                    X-RAY IMAGE

FIG.11A

EXPANSION
RECOGNITION IMAGE

FIG.11B

CONTRACTION
RECOGNITION IMAGE

FIG.12

EXPANDED-PORTION
CONFIRMATION IMAGE

FIG.14

RADIOGRAPHIC IMAGING APPARATUS

CROSS-REFERENCE TO RELATED APPLICATIONS

This application claims the benefit of priority to Japanese Patent Application No. 2018-213204 filed on Nov. 13, 2018. The entire contents of this application are hereby incorporated herein by reference.

BACKGROUND OF THE INVENTION

Field of the Invention

The present invention relates to a radiographic imaging apparatus, and more particularly, it relates to a radiographic imaging apparatus including a display that displays a processed image that has been subjected to image processing in an image processor.

Description of the Background Art

Conventionally, a radiographic imaging apparatus including a display that displays a processed image obtained by performing image processing on a radiographically captured radiation image in an image processor is known. Such a radiographic imaging apparatus is disclosed in Japanese Patent No. 5337525, for example.

Japanese Patent No. 5337525 discloses an X-ray diagnostic apparatus (radiographic imaging apparatus) including a display that displays an X-ray image (processed image) that has been subjected to image processing in an image processor. The image processor of the X-ray diagnostic apparatus disclosed in Japanese Patent No. 5337525 is configured to create the X-ray image that can be displayed on the display by performing the image processing including luminance value adjustment and size adjustment on X-ray image data obtained by converting the detection results of an X-ray detector that detects X-rays transmitted through a subject.

In the X-ray diagnostic apparatus disclosed in Japanese Patent No. 5337525, an operator introduces a catheter into the blood vessel of the subject while visually recognizing the X-ray image displayed on the display. Furthermore, in the X-ray diagnostic apparatus disclosed in Japanese Patent No. 5337525, the operator performs treatment by expanding a balloon introduced in a contracted state in a region to be treated.

However, in the X-ray diagnostic apparatus disclosed in Japanese Patent No. 5337525, when the treatment is performed on the blood vessel in the region to be treated, due to no mark indicating the region to be treated, it is difficult to confirm the region (dilated blood vessel portion) that has been treated with the balloon in the subject after the treatment. In other words, in the X-ray diagnostic apparatus disclosed in Japanese Patent No. 5337525, it is necessary to confirm a past dilated blood vessel portion by comparing a pre-treatment image and a post-treatment image or based on the operator's memory. Therefore, it is not possible to easily confirm the progress of the treatment by expansion of the balloon in the subject.

SUMMARY OF THE INVENTION

The present invention is intended to solve the above problem. The present invention aims to provide a radiographic imaging apparatus that enables an operator to easily confirm the progress of treatment in a subject by expansion of a balloon.

In order to attain the aforementioned object, a radiographic imaging apparatus according to an aspect of the present invention includes an image generator configured to generate a radiation image based on detection signals of radiation transmitted through a subject, an image processor configured to perform image processing on the radiation image generated by the image generator, and a display configured to display a processed image that has been subjected to the image processing in the image processor. The image processor is configured to perform control to create the processed image showing an expanded portion in which a balloon introduced into the subject is expanded.

As described above, the radiographic imaging apparatus according to this aspect of the present invention includes the image processor configured to perform control to create the processed image showing the expanded portion in which the balloon introduced into the subject is expanded. Accordingly, even when the treatment with the balloon is performed, the expanded portion of the subject in which the balloon is expanded can be confirmed after the treatment, and thus the progress of the treatment by expansion of the balloon in the subject can be easily confirmed.

In the aforementioned radiographic imaging apparatus according to this aspect, the image processor is preferably configured to perform control to acquire the expanded portion of the balloon based on an expansion recognition image in which expansion of the balloon introduced into the subject is recognized among radiation images generated by the image generator. Accordingly, expansion of the balloon can be automatically recognized by the image processor, and thus the burden on an operator during the treatment can be reduced. Furthermore, unlike the case in which another configuration such as a pressure gauge is provided in the radiographic imaging apparatus such that expansion of the balloon is recognized, the existing radiographic imaging apparatus can be used to acquire the expanded portion of the balloon without adding another configuration such as a pressure gauge, and thus it is possible to significantly reduce or prevent an increase in the size of the radiographic imaging apparatus and the complex configuration of the radiographic imaging apparatus.

In this case, the image processor is preferably configured to perform control to acquire the expansion recognition image based on a change in a pixel value of a portion of the radiation image showing the balloon and acquired based on a position of a balloon marker in the radiation image. Accordingly, the balloon marker can be clearly identified in the radiation image, and thus the portion of the radiation image showing the balloon can be accurately acquired. Consequently, the image processor can accurately recognize expansion of the balloon.

In the aforementioned radiographic imaging apparatus according to this aspect, the image processor is preferably configured to perform control to create the processed image by superimposing a figure along a shape of the balloon on the expanded portion of the balloon in the radiation image. Accordingly, the visibility of the expanded portion of the balloon in the processed image can be improved, and thus the progress of the treatment by expansion of the balloon in the subject can be more easily confirmed.

In the aforementioned radiographic imaging apparatus according to this aspect, the image processor is preferably configured to perform control to store the expanded portion of the balloon and create the processed image by showing the expanded portion of the balloon previously stored in the radiation image when the balloon is expanded a plurality of times. Accordingly, the operator can perform the treatment while confirming the past expanded portion of the balloon by referring to the processed image, and thus the treatment by expansion of the balloon in the subject can be performed smoothly.

In the aforementioned radiographic imaging apparatus according to this aspect, the image processor is preferably configured to perform control to create an expanded-portion confirmation image by showing the expanded portion of the balloon in a contrast image of the subject captured with contrast medium and generated prior to an expansion recognition image in which expansion of the balloon introduced into the subject is recognized among radiation images generated by the image generator. Accordingly, the expanded portion of the balloon is shown in the contrast image obtained by clearly imaging the blood vessel such that it is possible to confirm alignment between a stenotic portion of the blood vessel of the subject and the expanded portion of the balloon, and thus the treatment of the stenotic portion of the blood vessel of the subject can be performed more reliably.

In the aforementioned radiographic imaging apparatus according to this aspect, the image processor is preferably configured to perform control to correct the expanded portion of the balloon shown in the processed image based on detection of a displacement due to body movement of the subject or periodic movement of an object in the subject based on a comparison between a position of a feature point in an expansion recognition image in which expansion of the balloon introduced into the subject is recognized among radiation images generated by the image generator and a position of a feature point in the radiation image corresponding to the feature point in the expansion recognition image. Accordingly, even when the expanded portion of the balloon in the processed image is displaced due to body movement of the subject or periodic movement of the object in the subject, the expanded portion of the balloon can be corrected, and thus the more accurate expanded portion of the balloon can be taught to the operator.

In the aforementioned radiographic imaging apparatus according to this aspect, the image processor is preferably configured to perform control to store the processed image created by showing the expanded portion in an expansion recognition image in which expansion of the balloon introduced into the subject is recognized among radiation images generated by the image generator upon termination of acquisition of the radiation image of the subject when recognizing the expansion of the balloon introduced into the subject. Accordingly, the radiation image showing the expanded portion of the balloon can be reliably and easily stored as a record without any operation by the operator, and thus the progress of the treatment by expansion of the balloon in the subject can be reliably confirmed.

In the aforementioned radiographic imaging apparatus according to this aspect, the image processor is preferably configured to perform control to acquire an expansion duration time during which the balloon is expanded based on acquisition of an expansion recognition image in which expansion of the balloon introduced into the subject is recognized among radiation images generated by the image generator and acquisition of a contraction recognition image, which is the radiation image in which contraction of the balloon introduced into the subject is recognized, after the acquisition of the expansion recognition image, and store the expansion duration time in association with the expansion recognition image. Accordingly, the expansion duration time can be automatically acquired by the image processor without measurement by the operator using a stopwatch or the like, and thus the burden on the operator during the treatment can be reduced. Furthermore, it is possible to confirm excessive dilation or the lack of dilation of the stenotic portion of the blood vessel of the subject by the balloon, and thus the treatment of the stenotic portion of the blood vessel of the subject can be performed more safely.

In this case, the image processor is preferably configured to perform control to create the processed image showing supplementary information including the expansion duration time in addition to the expanded portion. Accordingly, the detailed progress of the treatment by expansion of the balloon in the subject can be confirmed together with the expanded portion, and thus the treatment of the stenotic portion of the blood vessel of the subject can be performed more smoothly.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

The configuration of an X-ray imaging apparatus 1 according to this embodiment is now described with reference to FIGS. 1 to 13. The X-ray imaging apparatus 1 is an apparatus that captures an X-ray image P (fluoroscopic image) obtained by imaging the inside of a subject T by radiating X-rays from the outside of the subject T such as a human body (performs X-ray fluoroscopic imaging). The X-ray imaging apparatus 1 is an example of a "radiographic imaging apparatus" in the claims. The X-rays are examples of "radiation" in the claims. The X-ray image P is an example of a "radiation image" in the claims. The fluoroscopic image refers to an image obtained by imaging the subject T with a dose lower than a predetermined dose.

Figure 1:
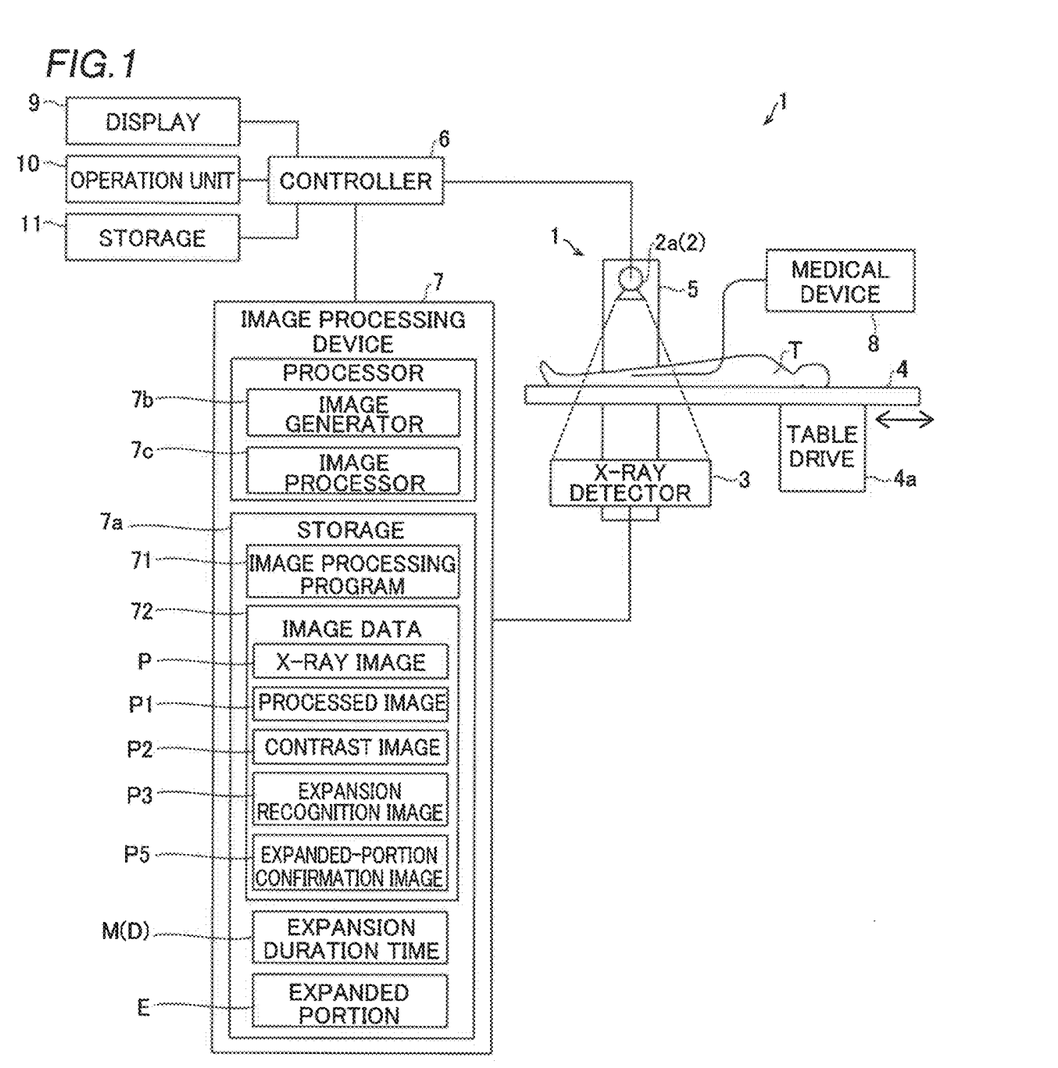
FIG. 1 is a block diagram showing the overall configuration of an X-ray imaging apparatus according to an embodiment.

As shown in FIG. 1, the X-ray imaging apparatus 1 includes an irradiator 2 that irradiates the subject T with X-rays and an X-ray detector 3 that detects the X-rays transmitted through the subject T. The irradiator 2 and the X-ray detector 3 face each other with a table 4, on which the subject T is placed, interposed therebetween. The irradiator 2 and the X-ray detector 3 are movably supported by a moving mechanism 5. The table 4 can be moved in a horizontal direction by a table drive 4a. An imaging region is moved by moving the irradiator 2, the X-ray detector 3, and the table 4 via the moving mechanism 5 and the table drive 4a. The imaging region refers to a region to be imaged in the subject T for examination and treatment.

The irradiator 2 includes an X-ray source 2a. The X-ray source 2a is an X-ray tube connected to a high-voltage generator (not shown) and configured to generate X-rays when a high voltage is applied thereto. The X-ray source 2a is arranged in such a manner that the X-ray emission direction thereof faces a detection surface of the X-ray detector 3. The irradiator 2 is connected to a controller 6. The controller 6 is configured or programmed to control the irradiator 2 in accordance with preset imaging conditions such as a tube voltage, a tube current, and an X-ray irradiation time interval, and to generate X-rays from the X-ray source 2a.

The X-ray detector 3 is configured to detect the X-rays radiated from the irradiator 2 and transmitted through the subject T, and to output a detection signal corresponding to the detected X-ray intensity. The X-ray detector 3 is a flat panel detector (FPD), for example. The X-ray detector 3 is configured to output a detection signal having a predetermined resolution to an image processing device 7. The image processing device 7 is configured to acquire the detection signal from the X-ray detector 3, and to generate the X-ray image P (processed image P1; see FIG. 3).

Figure 2:
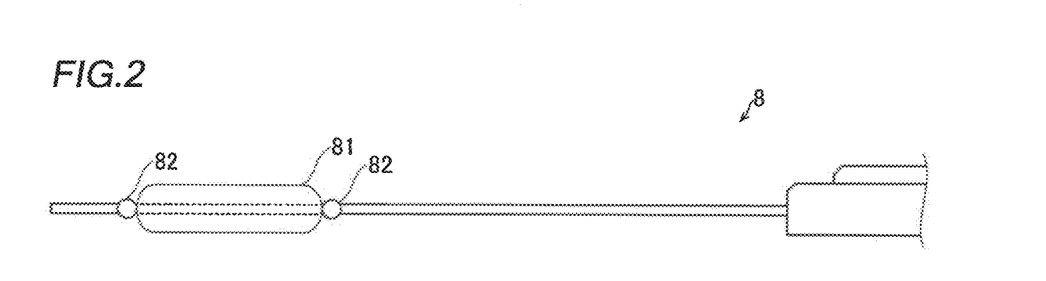
FIG. 2 is a schematic view showing a medical device including a balloon in the X-ray imaging apparatus according to the embodiment.

As shown in FIG. 2, a medical device 8 (balloon catheter) introduced into the subject T includes a balloon 81 for blood vessel treatment. The balloon 81 is used for balloon angioplasty (treatment) for dilating a blood vessel narrowed due to arteriosclerosis or cholesterol clogging and restoring blood flow, for example. In the balloon angioplasty, the medical device 8 including a guide wire therein is introduced into the blood vessel of the subject T, and the medical device 8 reaches a region to be treated of the blood vessel via the blood vessel to perform treatment. In the balloon angioplasty, treatment may be performed by bringing the medical device 8 including the balloon 81 coated with a drug on the surface thereof to the region to be treated of the blood vessel and then expanding the balloon 81 to bring the balloon 81 into contact with the inner wall of the blood vessel so as to apply the drug on the surface of the balloon 81 to the inner wall of the blood vessel.

The balloon 81 is made of resin (such as polyethylene). The balloon 81 has a bag shape that expands (inflates) by injecting air or sterilized water. The balloon 81 is disposed in the region (stenotic portion) to be treated of the blood vessel, and dilates the narrowed blood vessel by expanding. The resin balloon 81 has lower X-ray permeability than the surrounding body tissue and blood vessels. Thus, the resin balloon 81 is shown darker than the surrounding body tissue and blood vessels in the X-ray image P.

The balloon 81 is provided with a pair of balloon markers 82 having low X-ray permeability (or being radiopaque) as marks. The pair of balloon markers 82 are provided at one end and the other end of the balloon 81 in a longitudinal direction, respectively. The pair of balloon markers 82 are shown darker than the surrounding body tissues and blood vessels in the X-ray image P.

The treatment mentioned above indicates that the blood vessel is dilated at the region to be treated of the blood vessel in the subject T with the balloon 81 for blood vessel treatment.

As shown in FIG. 1, the X-ray imaging apparatus 1 includes the controller 6 that controls the irradiator 2 and the image processing device 7 and drivingly controls the moving mechanism 5 and the table drive 4a. The controller 6 includes a central processing unit (CPU), a read-only memory (ROM) (not shown), a random access memory (RAM) (not shown), etc. The controller 6 functions as a controller that controls each portion of the X-ray imaging apparatus 1 when the CPU executes a predetermined control program.

The X-ray imaging apparatus 1 includes a display 9, an operation unit 10, and a storage 11. The display 9 is a monitor such as a liquid crystal display. The display 9 displays the processed image P1 (see FIG. 3) that has been subjected to image processing in an image processor 7c described below. The operation unit 10 includes a keyboard and a mouse, a touch panel, or another control, for example. The storage 11 is a storage device such as a hard disk drive. The controller 6 is configured or programmed to control the display 9 to display an image generated by the image processing device 7. The controller 6 is configured or programmed to receive an input operation via the operation unit 10. The storage 11 is configured to store image data, the imaging conditions, and various set values. Each of the display 9 and the operation unit 10 may be provided in the image processing device 7.

The image processing device 7 includes a storage 7a such as a ROM and a RAM, and a processor such as a CPU or a graphics processing unit (GPU), for example. That is, the image processing device 7 is configured to cause the processor to execute an image processing program 71 stored in the storage 7a. The image processing device 7 may be configured integrally with the controller 6 by causing the same hardware (CPU) as the controller 6 to execute the image processing program 71.

The storage 7a stores the image processing program 71 for causing a computer to function as the image processing device 7. The storage 7a is configured to store image data 72 including X-ray images P continuously generated by an image generator 7b described below, the processed image P1 created by the image processor 7c described below, a contrast image P2 obtained by imaging a blood vessel by injecting contrast medium, an expansion recognition image P3 (described below) among the X-ray images P, and an expanded-portion confirmation image P5 described below. The storage 7a is configured to store the positions of the X-ray source 2a, the X-ray detector 3, and the table 4 and pixel values including the background pixel values of the X-ray images P.

The image processing device 7 has the functions of the image generator 7b and the image processor 7c by executing the image processing program 71. The image generator 7b and the image processor 7c may be configured separately with dedicated processors.

The image generator 7b is configured to generate the X-ray image P based on detection signals of the X-rays transmitted through the subject T. The image generator 7b continuously generates the X-ray images P in the form of a moving image based on the detection signals from the X-ray detector 3. That is, X-rays are intermittently radiated from the irradiator 2 to the subject T at predetermined time intervals, and the X-rays transmitted through the subject T are sequentially detected by the X-ray detector 3. The image generator 7b continuously generates the X-ray images P at a predetermined frame rate by imaging the detection signals sequentially output from the X-ray detector 3. The frame rate may be about 15 fps to 30 fps, for example.

(Image Processor)

Figure 3:
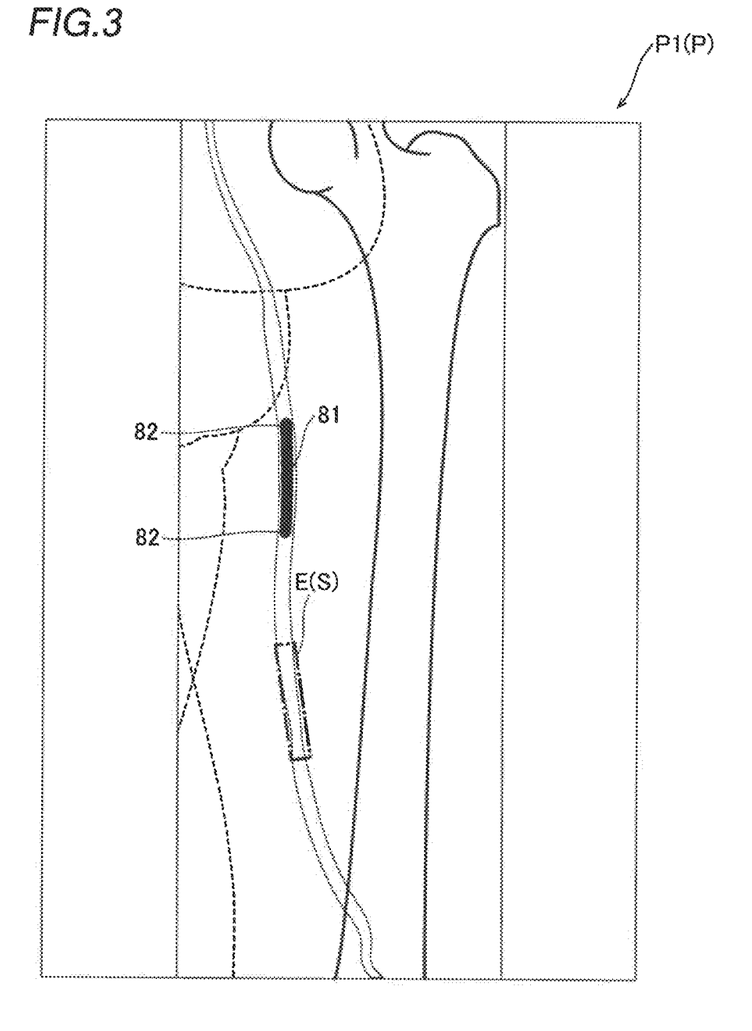
FIG. 3 is a schematic view showing a processed image that shows an expanded portion of the balloon in the X-ray imaging apparatus according to the embodiment.

As shown in FIG. 3, the image processor 7c is configured to perform image processing on the X-ray image P generated by the image generator 7b. Specifically, the image processor 7c according to this embodiment is configured to perform control to create the processed image P1 by superimposing a figure S (frame) along the shape of the balloon 81 on an expanded portion E of the balloon 81 in the X-ray image P. That is, the image processor 7c is configured to create the processed image P1 by detecting blood vessel dilation using the balloon 81 from the X-ray image P and showing the detected dilated portion of the blood vessel as the past expanded portion E of the balloon 81 in the X-ray image P. The controller 6 is configured or programmed to display, on the display 9 (see FIG. 1), the processed image P1 created by the image processor 7c and showing the expanded portion E in which the balloon 81 introduced into the subject T is expanded.

In the image processor 7c, processing described below is performed in order to create the processed image P1 showing the expanded portion E in which the balloon 81 is expanded. The case in which the balloon angioplasty (treatment) is performed on the lower limb is described below as an example.

<Recognition of Expanded Portion of Balloon>

Figure 4:
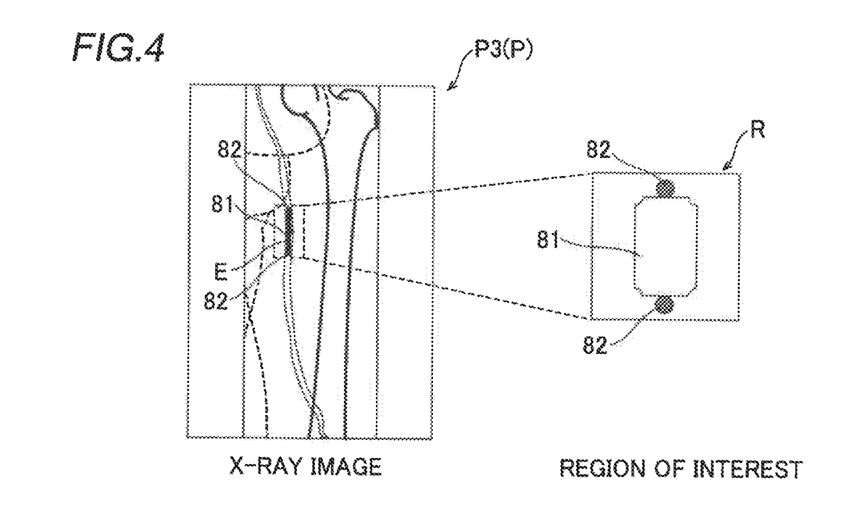
FIG. 4 is a schematic view showing an X-ray image and a region of interest of the X-ray image in the X-ray imaging apparatus according to the embodiment.
Figure 5:
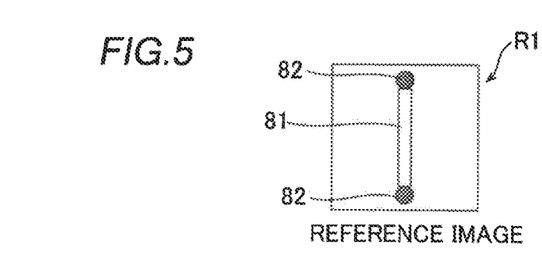
FIG. 5 is a schematic view showing a reference image in the X-ray imaging apparatus according to the embodiment.
Figure 6:
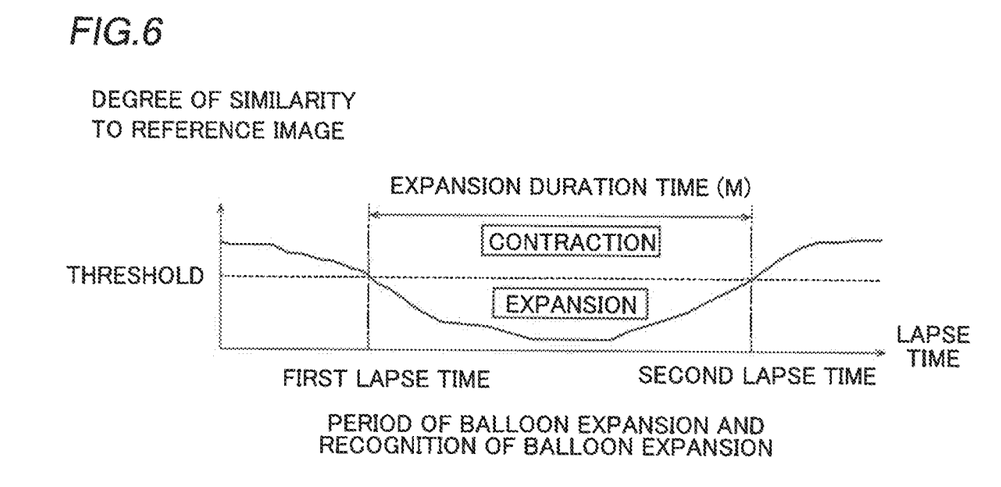
FIG. 6 is a graph showing a period of balloon expansion and recognition of balloon expansion in the X-ray imaging apparatus according to the embodiment.
Figure 7A:
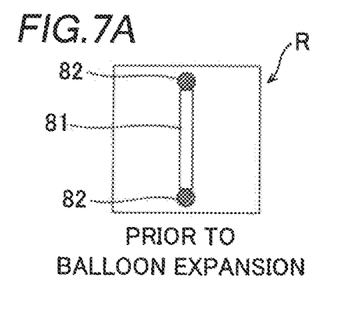
FIG. 7A is a schematic view showing the state of the region of interest in the X-ray image prior to balloon expansion.
Figure 7B:
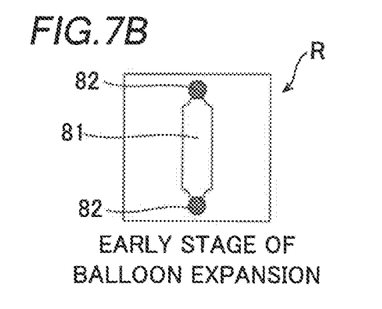
FIG. 7B is a schematic view showing the state of the region of interest in the X-ray image at the early stage of balloon expansion.
Figure 7C:
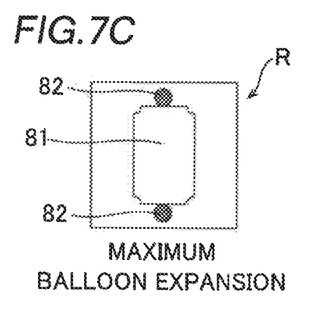
FIG. 7C is a schematic view showing the state of the region of interest in the X-ray image at the maximum balloon expansion.
Figure 7D:
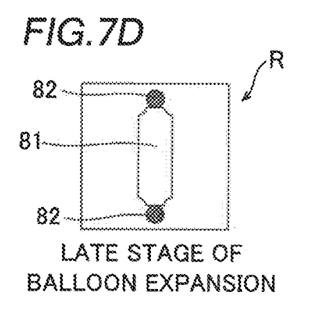
FIG. 7D is a schematic view showing the state of the region of interest in the X-ray image at the late stage of balloon expansion.
Figure 7E:
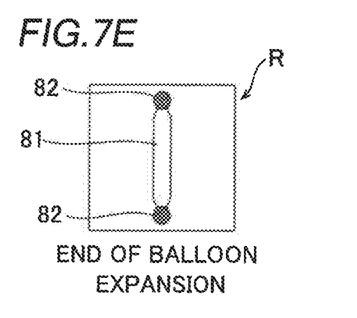
FIG. 7E is a schematic view showing the state of the region of interest in the X-ray image at the end of balloon expansion.

As shown in FIGS. 4 to 6, the image processor 7c is configured to perform control to acquire the expanded portion E of the balloon 81 based on the expansion recognition image P3 in which expansion of the balloon 81 introduced into the subject T is recognized among the X-ray images P generated by the image generator 7b. That is, the image processor 7c is configured to select the expansion recognition image P3, which is an X-ray image P showing expansion of the balloon 81, from a plurality of X-ray images P generated by the image generator 7b.

Specifically, the image processor 7c is configured to perform control to acquire the expansion recognition image P3 based on a change in the pixel value of a portion of the X-ray image P showing the balloon 81 and acquired based on the positions of the pair of balloon markers 82 in the X-ray image P. That is, the image processor 7c is configured to detect the pair of balloon markers 82 from the continuously collected X-ray images P, and recognize expansion and contraction of the balloon 81 based on a change in the pixel value of a portion between the pair of balloon markers 82.

Recognition of expansion and contraction of the balloon 81 is now described in detail.

As shown in FIG. 4, the image processor 7c is configured to create a region of interest R having a certain size from the detection positions of the pair of balloon markers 82 when the pair of balloon markers 82 are detected from the collected X-ray images P. As shown in FIG. 5, the image processor 7c is configured to create a reference image R1 obtained by averaging pixel values of respective regions of interest R in a plurality of collected X-ray images P. Among the collected X-ray images P, the number of X-ray images P with the balloon 81 contracted is larger than the number of X-ray images P with the balloon 81 expanded, and thus the reference image R1 has pixel values smaller than the pixel values of the X-ray image P with the balloon 81 contracted and larger than the pixel values of the X-ray image P with the balloon 81 expanded.

The image processor 7c is configured to perform control to acquire the expansion recognition image P3, which is the X-ray image P with the balloon 81 expanded among the plurality of images, based on the degree of similarity between the created reference image R1 and the respective regions of interest R in the plurality of collected X-ray images P. That is, the image processor 7c is configured to recognize expansion of the balloon 81 when a difference between the average value of the pixel values of the respective regions of interest R in the plurality of X-ray images P and the average value of the pixel values of the created reference image R1 is smaller than a threshold, and recognize contraction of the balloon 81 when the difference is equal to or larger than the threshold.

The image processor 7c may recognize expansion and contraction of the balloon 81 based on a correlation coefficient between the created reference image R1 and the respective regions of interest R in the plurality of collected X-ray images P, for example. Furthermore, the degree of similarity between the respective regions of interest R in the plurality of X-ray images P and the created reference image R1 may be obtained by another known method.

As shown in FIG. 6, the image processor 7c is configured to recognize the state (see FIG. 7A, for example) of the balloon 81 as a contracted state until a first lapse time has elapsed. The image processor 7c is configured to recognize the state (see FIGS. 7B to 7D, for example) of the balloon 81 from the first lapse time to a second lapse time as an expanded state. The image processor 7c is configured to recognize the state (see FIG. 7E, for example) of the balloon 81 as a contracted state after the second lapse time has elapsed.

In this manner, the image processor 7c acquires the expansion recognition image P3 from the collected X-ray images P by recognizing expansion and contraction of the balloon 81. Then, the image processor 7c acquires a portion from one of the pair of balloon markers 82 to the other of the pair of balloon markers 82 as the expanded portion E.

<Correction of Expanded Portion>

Figure 8:
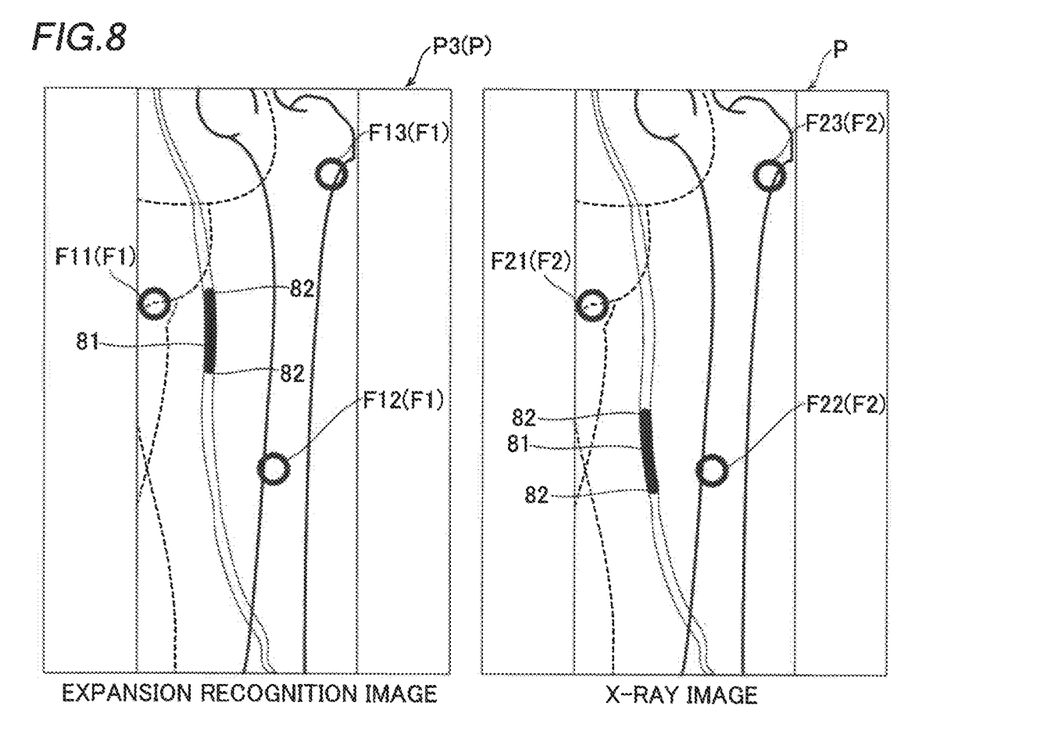
FIG. 8 is a schematic view showing an expansion recognition image showing feature points and an X-ray image showing the feature points in the X-ray imaging apparatus according to the embodiment.
Figure 9:
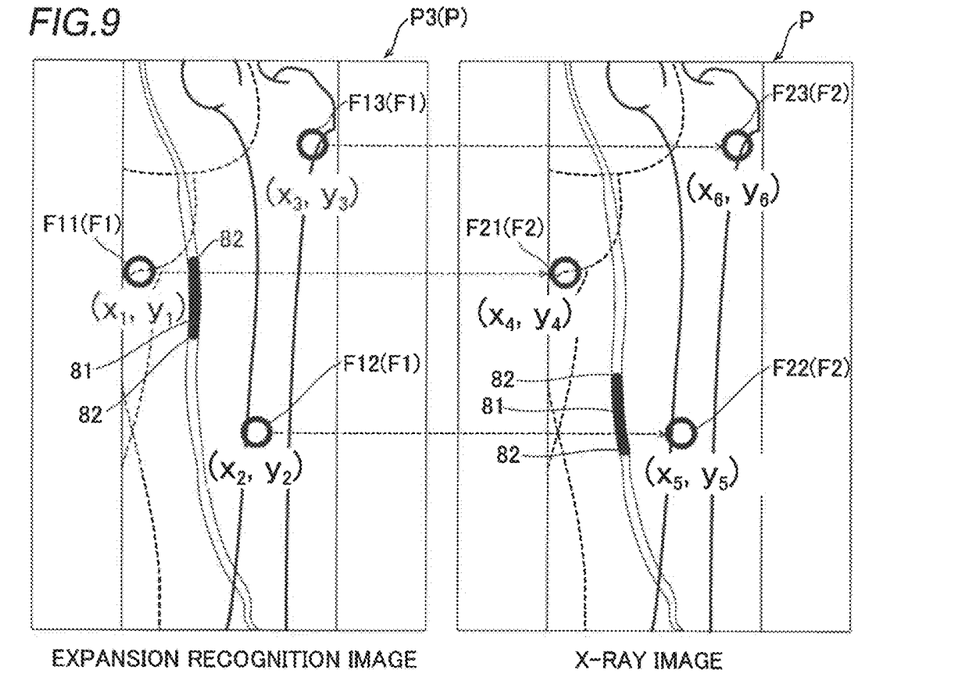
FIG. 9 is a schematic view showing a state in which the feature points of the expansion recognition image and the feature points of the X-ray image are associated with each other in the X-ray imaging apparatus according to the embodiment.
Figure 10:
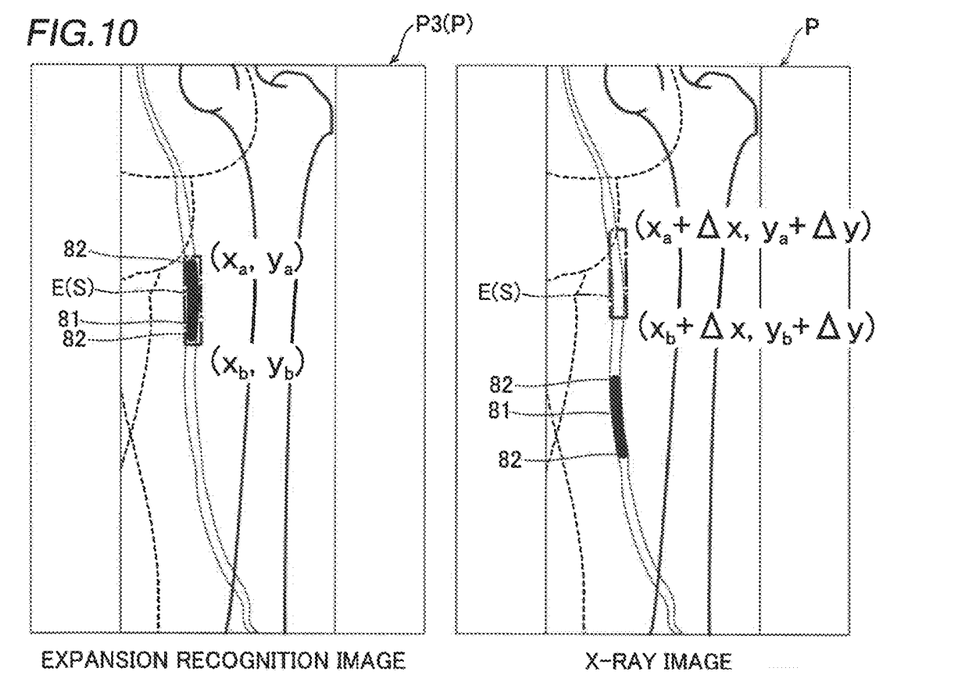
FIG. 10 is a schematic view showing the expanded portion in the expansion recognition image and a corrected expanded portion in the X-ray image in the X-ray imaging apparatus according to the embodiment.

As shown in FIGS. 8 to 10, the image processor 7c is configured to perform control to correct the expanded portion E of the balloon 81 shown in the processed image P1 in accordance with the amount of deviation between feature points F1 in the expansion recognition image P3 and feature points F2 in the X-ray image P corresponding to the feature points F1 in the expansion recognition image P3. That is, the image processor 7c is configured to perform control to correct the expanded portion E of the balloon 81 shown in the processed image P1 based on detection of a displacement due to body movement of the subject T based on comparisons between the positions of the feature points F1 in the expansion recognition image P3 and the positions of the feature points F2 in the X-ray image P corresponding to the feature points F1 in the expansion recognition image P3.

The feature points F1 and F2 refer to portions of the X-ray images P including the expansion recognition image P3 in which the pixel values suddenly decrease from surrounding pixel values. Furthermore, the body movement refers to the movement of the subject T due to a feeling of strangeness felt when the balloon 81 is expanded or the contrast medium is injected.

Specifically, the image processor 7c is configured to perform control to correct the expanded portion E of the balloon 81 shown in the processed image P1 by the average value of the differences between a plurality of feature points F1 in the expansion recognition image P3 and a plurality of feature points F2 in the X-ray image P respectively corresponding to the plurality of feature points F1 in the expansion recognition image P3.

Correction of the expanded portion E of the balloon 81 is now described in detail.

As shown in FIG. 8, the image processor 7c is configured to extract the plurality of (three) feature points F1 (hereinafter referred to as a first feature point F11, a second feature point F12, and a third feature point F13) from the expansion recognition image P3 based on the pixel values of the expansion recognition image P3. The image processor 7c is configured to extract the plurality of (three) feature points F2 (hereinafter referred to as a fourth feature point F21, a fifth feature point F22, and a sixth feature point F23) respectively corresponding to the first feature point F11, the second feature point F12, and the third feature point F13 based on the pixel values of the X-ray image P. Here, the X-ray image P refers to an X-ray image P in which information about the expansion portion E recognized in the expansion recognition image P3 is to be illustrated.

As shown in FIG. 9, the image processor 7c is configured to associate the first feature point F11, the second feature point F12, and the third feature point F13 extracted from the expansion recognition image P3 with the fourth feature point F21, the fifth feature point F22, and the sixth feature point F23 extracted from the X-ray image P by feature amount matching. Furthermore, the image processor 7c is configured to acquire a first displacement ($\Delta x_1$, $\Delta y_1$) between the first feature point F11 ($x_1$, $y_1$) and the fourth feature point F21 ($x_4$, $y_4$) with reference to the upper left corner of the image, for example. Similarly, the image processor 7c is configured to acquire a second displacement ($\Delta x_2$, $\Delta y_2$) between the second feature point F12 ($x_2$, $y_2$) and the fifth feature point F22 ($x_5$, $y_5$) and a third displacement ($\Delta x_3$, $\Delta y_3$) between the third feature point F13 ($x_3$, $y_3$) and the sixth feature point F23 ($x_6$, $y_6$). The average value of the first displacement, the second displacement, and the third displacement is defined as an average displacement ($\Delta x$, $\Delta y$).

As shown in FIG. 10, the image processor 7c is configured to correct the position of one of the pair of balloon markers 82 by adding the average displacement ($\Delta x$, $\Delta y$) to the position ($x_a$, $y_a$) of one of the pair of balloon markers 82 in the expansion recognition image P3. In addition, the image processor 7c is configured to correct the position of the other of the pair of balloon markers 82 by adding the average displacement ($\Delta x$, $\Delta y$) to the position ($x_b$, $y_b$) of the other of the pair of balloon markers 82 in the expansion recognition image P3. Accordingly, the image processor 7c is configured to correct the position of the expanded portion E based on the corrected positions of the pair of balloon markers 82 and show the expanded portion E in the X-ray image P.

In this manner, the image processor 7c corrects the expanded portion E based on information about the pixel values including the background pixel values of the X-ray image P and the expansion recognition image P3 stored in the storage 7a. Note that the method of correcting the expanded portion E described above is only an example, and the expanded portion E may be corrected by another known method.

The image processor 7c is preferably configured to correct the expanded portion E in the X-ray image P based on differences between the positions of the X-ray source 2a, the X-ray detector 3, and the table 4 at the time of capturing the expansion recognition image P3, and the positions of the X-ray source 2a, the X-ray detector 3, and the table 4 at the time of capturing the X-ray image P. The image processor 7c is preferably configured to correct the expanded portion E in the X-ray image P based on a difference between the magnification of the expansion recognition image P3 and the magnification of the X-ray image P.

<Time Measurement>

Figure 11A:
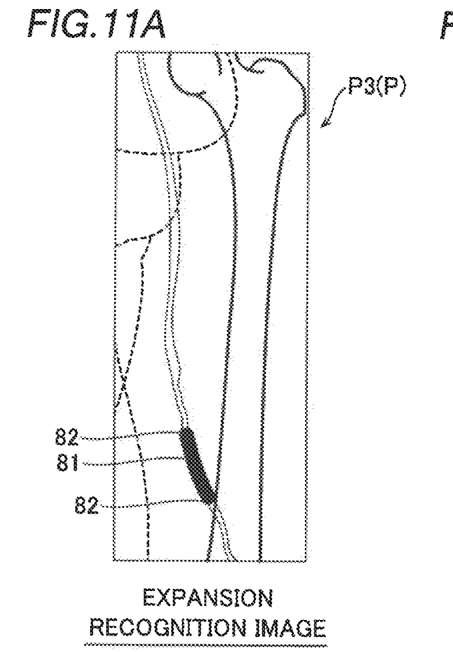
FIG. 11A is a schematic view showing the expansion recognition image.
Figure 11B:
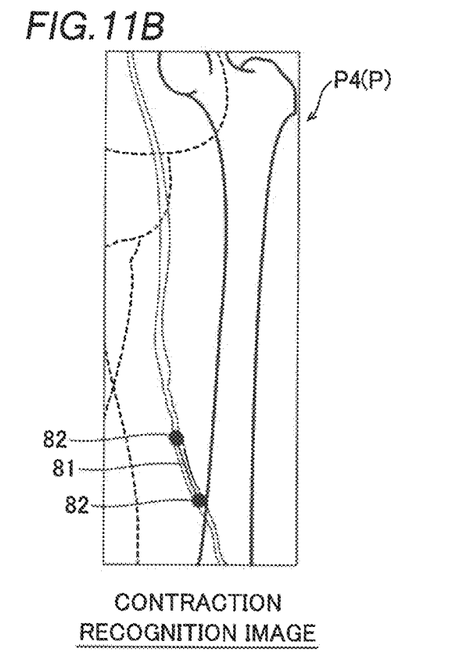
FIG. 11B is a schematic view showing a contraction recognition image.

As shown in FIGS. 11A and 11B, the image processor 7c is configured to acquire an expansion duration time M (see FIG. 6) during which the balloon 81 is expanded based on acquisition of the expansion recognition image P3 and acquisition of a contraction recognition image P4, which is an X-ray image P in which contraction of the balloon 81 introduced into the subject T is recognized, after the acquisition of the expansion recognition image P3, and to control the storage 7a to store the expansion duration time M in association with the expansion recognition image P3.

Specifically, the image processor 7c is configured to control the storage 7a to store a difference between a time point at which the degree of similarity between the region of interest R in the X-ray image P and the reference image R1 becomes smaller than a threshold and a time point at which the degree of similarity between the region of interest R in the X-ray image P and the reference image R1 becomes equal to or larger than the threshold as the expansion duration time M.

<Auto Save>

The image processor 7c is configured to control the storage 7a to store the processed image P1 created by showing the expanded portion E in the expansion recognition image P3 upon termination of acquisition of the X-ray image P of the subject T when recognizing expansion of the balloon 81 introduced into the subject T. Specifically, the image processor 7c is configured to arbitrarily store the X-ray image P (fluoroscopic image) in the storage 7a based on an operator's instruction, but is configured to always store, in the storage 7a, the processed image P1 created by showing the expanded portion E in the expansion recognition image P3 as a fluoroscopic record after treatment of the subject T when recognizing expansion of the balloon 81 in the region to be treated. The fluoroscopic record refers to an X-ray image P (fluoroscopic image) stored in the storage 7a when the subject T is irradiated with X-rays to capture the X-ray image P (fluoroscopic image).

<Expanded-Portion Confirmation Image>

Figure 12:
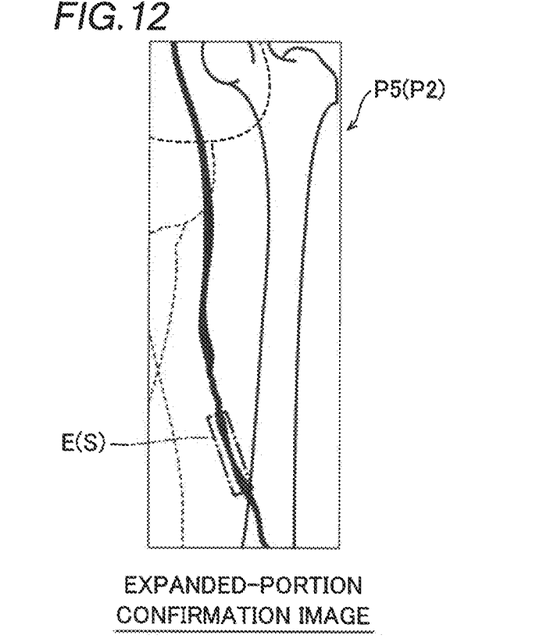
FIG. 12 is a schematic view showing an expanded-portion confirmation image created by showing the expanded portion of the balloon in a contrast image in the X-ray imaging apparatus according to the embodiment.

As shown in FIG. 12, the image processor 7c is configured to perform control to create the expanded-portion confirmation image P5 by showing the expanded portion E of the balloon 81 in the contrast image P2 of the subject T generated prior to the expansion recognition image P3.

Specifically, the image processor 7c is configured to perform control to acquire the contrast image P2 acquired before the balloon 81 is introduced into the subject T and stored in the storage 7a, and create the expanded-portion confirmation image P5 by displaying the figure S along the shape of the balloon 81 on the expanded portion E of the balloon 81 in the acquired contrast image P2. The image processor 7c is configured to perform control to create the expanded-portion confirmation image P5 when recognizing expansion of the balloon 81 introduced into the subject T. The controller 6 is configured or programmed to display the expanded-portion confirmation image P5 created by the image processor 7c on the display 9. The expanded-portion confirmation image P5 is stored in the storage 7a.

<Plurality of Expanded Portions>

Figure 13A:
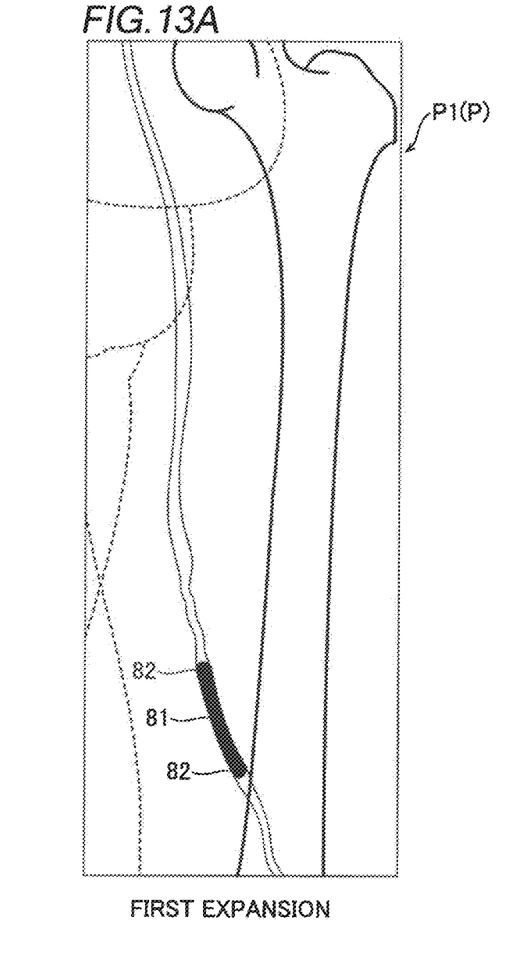
FIG. 13A is a schematic view of the processed image at the time of the first expansion of the balloon.
Figure 13B:
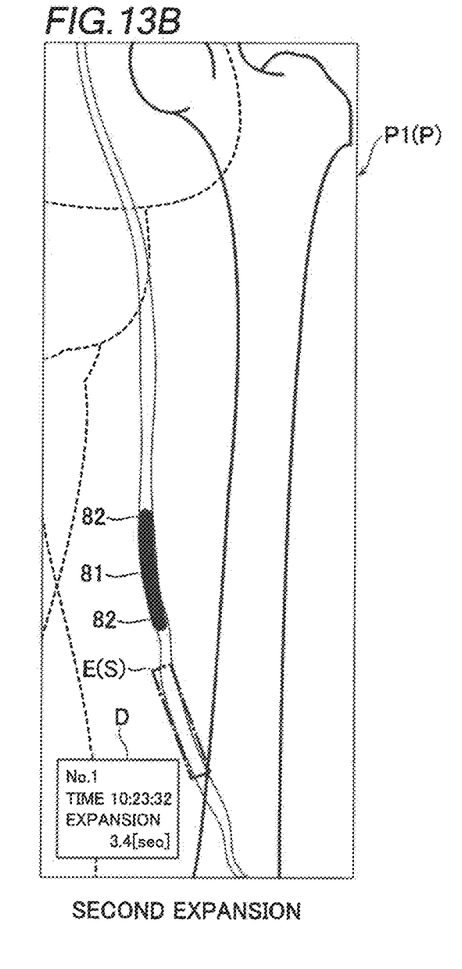
FIG. 13B is a schematic view of the processed image at the time of the second expansion of the balloon.
Figure 13C:
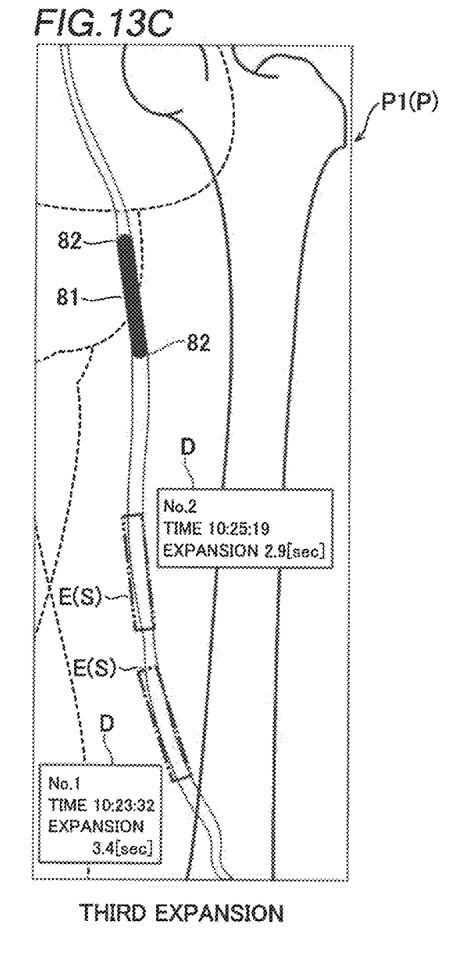
FIG. 13C is a schematic view of the processed image at the time of the third expansion of the balloon.

As shown in FIGS. 13A to 13C, the image processor 7c is configured to control the storage 7a to store the expanded portion E of the balloon 81 and perform control to create the processed image P1 by showing, in the X-ray image P, the previous (first and second) expanded portions E of the balloon 81 stored in the storage 7a when the balloon 81 is expanded a plurality of times (three times).

Specifically, the image processor 7c is configured to control the storage 7a to store the expanded portion E of the balloon 81 in association with the expansion recognition image P3 every time the balloon 81 is expanded, and to perform control to create the processed image P1 in which the figure S along the shape of the balloon 81 is superimposed on all of the expanded portions E of the balloon 81 stored in the past in the storage 7a. The controller 6 is configured or programmed to control the display 9 to display the processed image P1 created by superimposing the figure S along the shape of the balloon 81 on all of the expanded portions E of the balloon 81 stored in the past in the storage 7a by the image processor 7c.

That is, as shown in FIG. 13A, the image processor 7c stores, in the storage 7a, the first expanded portion E of the balloon 81 in association with the first expansion recognition image P3 when the first expansion of the balloon 81 is performed.

As shown in FIG. 13B, the image processor 7c is configured to perform control to create the processed image P1 in which the figure S along the shape of the balloon 81 is superimposed on the expanded portion E of the balloon 81 stored first in the storage 7a between the end of the first expansion of the balloon 81 and the end of the second expansion of the balloon 81. The controller 6 is configured or programmed to control the display 9 to display the processed image P1 created by the image processor 7c. When the second expansion of the balloon 81 is performed, the image processor 7c stores, in the storage 7a, the second expanded portion E of the balloon 81 in association with the second expansion recognition image P3.

As shown in FIG. 13C, the image processor 7c is configured to perform control to create the processed image P1 in which the figure S along the shape of the balloon 81 is superimposed on each of the first expanded portion E of the balloon 81 and the second expanded portion E of the balloon 81 stored in the storage 7a between the end of the second expansion of the balloon 81 and the end of the third expansion of the balloon 81. The controller 6 is configured or programmed to control the display 9 to display the processed image P1 created by the image processor 7c. When the third expansion of the balloon 81 is performed, the image processor 7c stores, in the storage 7a, the third expanded portion E of the balloon 81 in association with the third expansion recognition image P3.

<Supplementary Information>

As shown in FIGS. 13B and 13C, the image processor 7c is configured to perform control to create the processed image P1 showing supplementary information D including the expansion duration time M in addition to the expanded portion E. Specifically, the image processor 7c is configured to control the storage 7a to store the supplementary information D including the expanded portion E of the balloon 81 and the expansion duration time M when the balloon 81 is expanded a plurality of times. In addition, the image processor 7c is configured to perform control to create the processed image P1 by showing, in the X-ray image, the previous expanded portions E of the balloon 81 stored in the storage 7a and the supplementary information D associated with the previous expanded portions E of the balloon 81. The supplementary information D is shown at a position corresponding to the expanded portion E of the balloon 81.

The supplementary information D refers to information related to treatment for dilating the blood vessel at the region to be treated of the blood vessel in the subject T using the balloon 81 for blood vessel treatment. That is, the term "supplementary information D" indicates a concept including not only the expansion duration time M but also an expansion time (first lapse time) at which the degree of similarity between the region of interest R in the X-ray image P and the reference image R1 becomes smaller than the threshold, an arbitrary comment of the operator, a number or a color indicating the order of treatment, etc.

(Balloon-Expanded Portion Display Processing)

Balloon-expanded portion display processing is now described with reference to FIG. 14. The balloon-expanded portion display processing is processing for showing the expanded portion E (balloon-expanded portion) of the subject T, in which treatment by expansion of the balloon 81 is performed, in the X-ray image P, for example.

Figure 14:
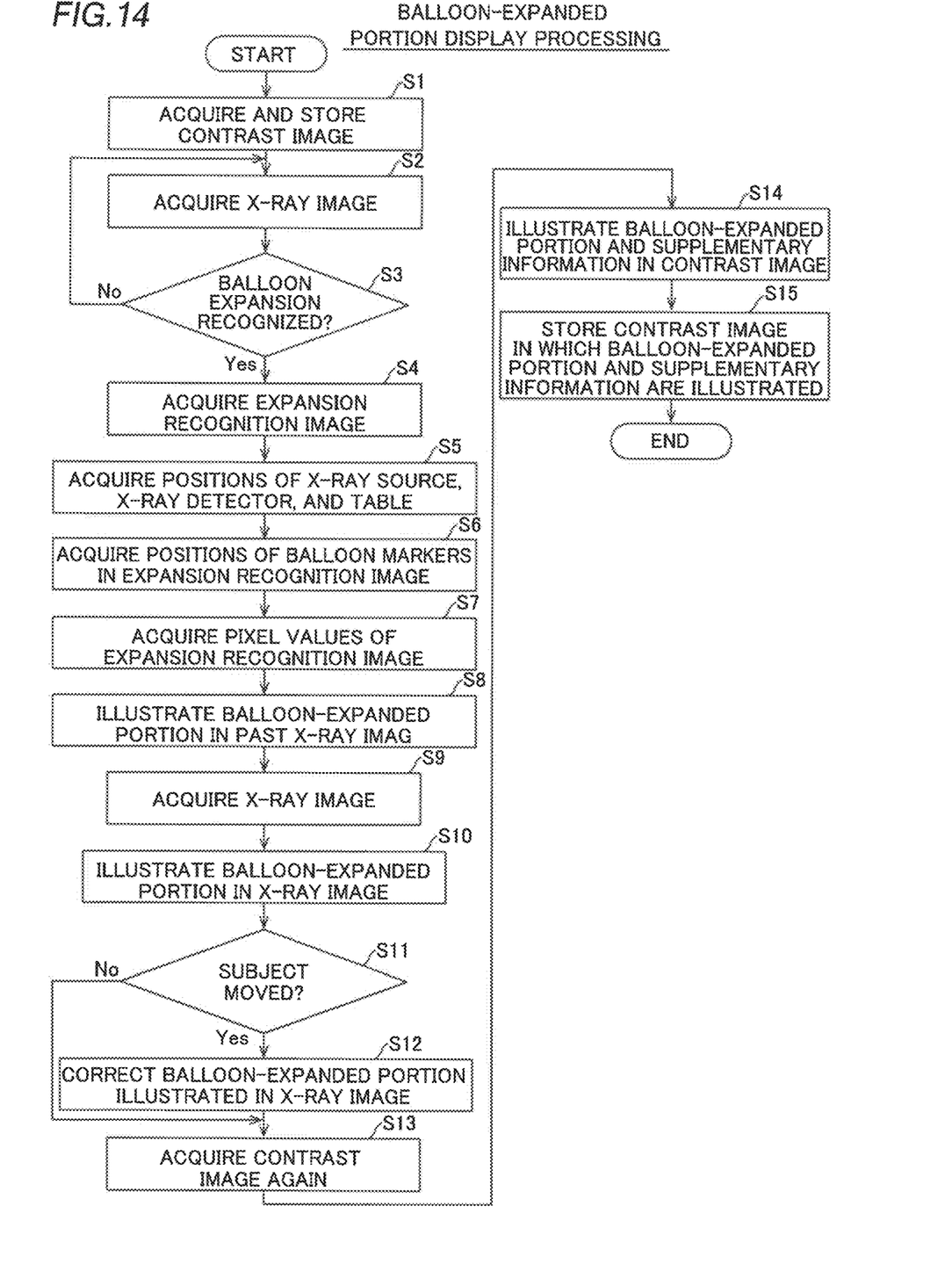
FIG. 14 is a flowchart showing balloon-expanded portion display processing in the X-ray imaging apparatus according to the embodiment.

As shown in FIG. 14, in step S1, the operator injects the contrast medium such that in the image processing device 7, the image processor 7c acquires and stores the contrast image P2. Then, after the operator specifies the region to be treated (stenotic portion) of the subject T, the region to be treated of the subject T is treated. In step S2, in the image processing device 7, the image processor 7c acquires the X-ray image P obtained by imaging the detection signals of the X-rays transmitted through the subject T in the X-ray detector 3 by the image generator 7b. In step S3, in the image processing device 7, the image processor 7c determines whether or not expansion of the balloon 81 has been recognized. That is, in the image processing device 7, the image processor 7c recognizes expansion of the balloon 81 from a change in pixel value in the region of interest R with reference to the pair of balloon markers 82. When expansion of the balloon 81 is recognized, the image processing device 7 advances to step S4, and when expansion of the balloon 81 is not recognized, the image processing device 7 returns to step S2.

In step S4, in the image processing device 7, the image processor 7c acquires the expansion recognition image P3 (X-ray image P) based on the recognition of the expansion of the balloon 81. At this time, in the image processing device 7, the image processor 7c stores, in the storage 7a, the time at which the expansion of the balloon 81 is recognized as the expansion duration time M. In step S5, in the image processing device 7, the image processor 7c acquires the positions of the X-ray source 2a, the X-ray detector 3, and the table 4. Then, in the image processing device 7, the image processor 7c stores the positions of the X-ray source 2a, the X-ray detector 3, and the table 4 in the storage 7a. In step S6, in the image processing device 7, the image processor 7c acquires the positions of the balloon markers 82 in the expansion recognition image P3. In step S7, in the image processing device 7, the image processor 7c acquires the pixel values of the expansion recognition image P3.

In step S8, in the image processing device 7, the image processor 7c illustrates the balloon-expanded portion (expanded-portion E) in the past image (contrast image P2) before expansion of the balloon 81. That is, the figure S along the shape of the balloon 81 is shown as the balloon-expanded portion (expanded portion E) in the contrast image P2 acquired at the beginning of treatment (before the balloon 81 is introduced into the body of the subject T). Then, the treatment of the region to be treated of the subject T is resumed. That is, the operator treats another region to be treated of the subject T. In step S9, in the image processing device 7, the image processor 7c acquires the X-ray image P generated by the image generator 7b. In step S10, in the image processing device 7, the image processor 7c illustrates the balloon-expanded portion in the X-ray image P.

In step S11, in the image processing device 7, the image processor 7c determines whether or not there is movement (body movement) of the subject T. When there is movement of the subject T, the image processing device 7 advances to step S12, and when there is no movement of the subject T, the image processing device 7 advances to step S13. In step 12, in the image processing device 7, the image processor 7c corrects the balloon-expanded portion illustrated in the X-ray image P by the amount of movement of the subject T. In step S13, the operator injects the contrast medium such that in the image processing device 7, the image processor 7c acquires the contrast image P2 again. That is, when the scheduled treatment is completed, the contrast image P2 is captured again by the operator.

In step S14, in the image processing device 7, the image processor 7c illustrates all the balloon-expanded portions and the supplementary information D in the contrast image P2 acquired again. In step S15, in the image processing device 7, the image processor 7c stores, in the storage 7a, the contrast image P2 in which the balloon-expanded portions and the supplementary information D are illustrated, and then the balloon-expanded portion display processing is terminated. That is, the contrast image P2 showing the balloon-expanded portions and the supplementary information D is stored in the storage 7a such that it can be used as a record of the treatment result.

Advantages of this Embodiment

According to this embodiment, the following advantages are obtained.

According to this embodiment, as described above, in the X-ray imaging apparatus 1, the image processor 7c is configured to perform control to create the processed image P1 showing the expanded portion E in which the balloon 81 introduced into the subject T is expanded. Accordingly, even when the treatment with the balloon 81 is performed, the expanded portion E of the subject T in which the balloon 81 is expanded can be confirmed after the treatment, and thus the progress of the treatment by expansion of the balloon 81 in the subject T can be easily confirmed.

According to this embodiment, as described above, the image processor 7c is configured to perform control to acquire the expanded portion E of the balloon 81 based on the expansion recognition image P3. Accordingly, expansion of the balloon 81 can be automatically recognized by the image processor 7c, and thus the burden on the operator during the treatment can be reduced. Furthermore, unlike the case in which another configuration such as a pressure gauge is provided in the X-ray imaging apparatus 1 such that expansion of the balloon 81 is recognized, the existing X-ray imaging apparatus 1 can be used to acquire the expanded portion of the balloon 81 without adding another configuration such as a pressure gauge, and thus it is possible to significantly reduce or prevent an increase in the size of the X-ray imaging apparatus 1 and the complex configuration of the X-ray imaging apparatus 1.

According to this embodiment, as described above, the image processor 7c is configured to perform control to acquire the expansion recognition image P3 based on the change in the pixel value of the portion of the X-ray image P showing the balloon 81 and acquired based on the positions of the balloon markers 82 in the X-ray image P. Accordingly, the balloon markers 82 can be clearly identified in the X-ray image P, and thus the portion of the X-ray image P showing the balloon 81 can be accurately acquired. Consequently, the image processor 7c can accurately recognize expansion of the balloon 81.

According to this embodiment, as described above, the image processor 7c is configured to perform control to create the processed image P1 by superimposing the figure S along the shape of the balloon 81 on the expanded portion E of the balloon 81 in the X-ray image P. Accordingly, the visibility of the expanded portion E of the balloon 81 in the processed image P1 can be improved, and thus the progress of the treatment by expansion of the balloon 81 in the subject T can be more easily confirmed.

According to this embodiment, as described above, the image processor 7c is configured to control the storage 7a to store the expanded portion E of the balloon 81 and perform control to create the processed image P1 by showing the previous expanded portions E of the balloon 81 stored in the storage 7a in the X-ray image P when the balloon 81 is expanded a plurality of times. Accordingly, the operator can perform the treatment while confirming the past expanded portion E of the balloon 81 by referring to the processed image P1, and thus the treatment by expansion of the balloon 81 in the subject T can be performed smoothly.

According to this embodiment, as described above, the image processor 7c is configured to perform control to create the expanded-portion confirmation image P5 by showing the expanded portion E of the balloon 81 in the contrast image P2. Accordingly, the expanded portion E of the balloon 81 is shown in the contrast image P2 obtained by clearly imaging the blood vessel such that it is possible to confirm alignment between the stenotic portion of the blood vessel of the subject T and the expanded portion E of the balloon 81, and thus the treatment of the stenotic portion of the blood vessel of the subject T can be performed more reliably.

According to this embodiment, as described above, the image processor 7c is configured to perform control to correct the expanded portion E of the balloon 81 shown in the processed image P1 based on detection of the displacement due to body movement of the subject T based on comparisons between the positions of the feature points F1 in the expansion recognition image P3 and the positions of the feature points F2 in the X-ray image P. Accordingly, even when the expanded portion E of the balloon 81 in the processed image P1 is displaced due to body movement of the subject T, the expanded portion E of the balloon 81 can be corrected, and thus the more accurate expanded portion E of the balloon 81 can be taught to the operator.

According to this embodiment, as described above, the image processor 7c is configured to control the storage 7a to store the processed image P1 created by showing the expanded portion E in the expansion recognition image P3 upon termination of acquisition of the X-ray image P of the subject T when recognizing expansion of the balloon 81 introduced into the subject T. Accordingly, the X-ray image P showing the expanded portion E of the balloon 81 can be reliably and easily stored as a record without any operation by the operator, and thus the progress of the treatment by expansion of the balloon 81 in the subject T can be reliably confirmed.

According to this embodiment, as described above, the image processor 7c is configured to perform control to acquire the expansion duration time M during which the balloon 81 is expanded based on acquisition of the expansion recognition image P3 and acquisition of the contraction recognition image P4, and control the storage 7a to store the expansion duration time M in association with the expansion recognition image P3. Accordingly, the expansion duration time M can be automatically acquired by the image processor 7c without measurement by the operator using a stopwatch or the like, and thus the burden on the operator during the treatment can be reduced. Furthermore, it is possible to confirm excessive dilation or the lack of dilation of the stenotic portion of the blood vessel of the subject T by the balloon 81, and thus the treatment of the stenotic portion of the blood vessel of the subject T can be performed more safely.

According to this embodiment, as described above, the image processor 7c is configured to perform control to create the processed image P1 showing the supplementary information D including the expansion duration time M in addition to the expanded portion E. Accordingly, the detailed progress of the treatment by expansion of the balloon 81 in the subject T can be confirmed together with the expanded portion E, and thus the treatment of the stenotic portion of the blood vessel of the subject T can be performed more smoothly.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while when the balloon angioplasty (treatment) is performed on the lower limb, the image processor 7c creates the processed image P1 showing the expanded portion E in which the balloon 81 is expanded in the aforementioned embodiment, the present invention is not limited to this. In the present invention, the image processor may alternatively create a processed image showing an expanded portion of a region other than the lower limb, in which the balloon is expanded.

While the image processor 7c performs control to create the processed image P1 by superimposing the figure S (frame) along the shape of the balloon 81 on the expanded portion E of the balloon 81 in the X-ray image P in the aforementioned embodiment, the present invention is not limited to this. In the present invention, the image processor may alternatively be configured to perform control to create the processed image by superimposing an arrow or a circle on the expanded portion of the balloon in the X-ray image.

While the image processor 7c is configured to perform control to acquire the expansion recognition image P3 based on the change in the pixel value of the portion of the X-ray image P showing the balloon 81 and acquired based on the positions of the pair of balloon markers 82 in the X-ray image P in the aforementioned embodiment, the present invention is not limited to this. In the present invention, the image processor may alternatively perform control to acquire the expansion recognition image based on a measurement value of a pressure gauge connected to the medical device or a change in pixel value due to balloon expansion.

While the balloon 81 is provided with the pair of (two) balloon markers 82 as marks in the aforementioned embodiment, the present invention is not limited to this. In the present invention, the balloon may alternatively be provided with one or three or more balloon markers as marks.

While the image processor 7c is configured to perform control to correct the expanded portion E of the balloon 81 shown in the processed image P1 based on detection of the displacement due to body movement of the subject T in the aforementioned embodiment, the present invention is not limited to this. The image processor may alternatively be configured to perform control to correct the expanded portion of the balloon shown in the processed image based on detection of a displacement due to an object such as a periodically moving organ (such as a heart) of the subject. That is, the image processor may be configured to acquire phase information based on periodic movement changes such as heartbeat and respiration by analyzing individual X-ray images. As a method for selecting an X-ray image with a phase that substantially matches the phase of the X-ray image, from which the phase information has been acquired, based on the phase information acquired from the X-ray image and specifying the position of the same object from the different X-ray images, the contents disclosed in detail in Japanese Patent Laid-Open No. 2017-094006 by the present applicant can be adopted. In this specification, the description of Japanese Patent Laid-Open No. 2017-094006 is cited by reference.

While the image processor 7c creates the processed image P1 by showing the expanded portion E in the X-ray image P generated by the image generator 7b when the subject T is exposed to X-rays in the aforementioned embodiment, the present invention is not limited to this. In the present invention, the image processor may alternatively create the processed image by showing the expanded portion in the collected X-ray images stored in the storage, a long image obtained by connecting a plurality of collected X-ray images stored in the storage, or a contrast image captured by the operator injecting the contrast medium.

While the image processor 7c is configured to extract the three feature points F1 from the expansion recognition image P3 based on the pixel values of the expansion recognition image P3 in the aforementioned embodiment, the present invention is not limited to this. In the present invention, the image processor may alternatively be configured to extract one, two, or four or more feature points from the expansion recognition image based on the pixel values of the expansion recognition image.

While the image processor 7c is configured to control the storage 7a to store the difference between the time point at which the degree of similarity between the region of interest R in the X-ray image P and the reference image R1 becomes smaller than the threshold and the time point at which the degree of similarity between the region of interest R in the X-ray image P and the reference image R1 becomes equal to or larger than the threshold as the expansion duration time M in the aforementioned embodiment, the present invention is not limited to this. In the present invention, the image processor may alternatively be configured to be able to change the expansion duration time when an instruction to change the expansion duration time is received from the operator in processing subsequent to acquisition of the expansion duration time.

While expansion of the balloon 81 is performed three times in the aforementioned embodiment, the present invention is not limited to this. In the present invention, the balloon expansion may alternatively be performed two or four times or more.

While the image processor 7c is configured to perform control to display the figure S along the shape of the balloon 81 as the expanded portion E in the contrast image P2 acquired at the beginning of the treatment (before the balloon 81 is introduced into the body of the subject T) in the aforementioned embodiment, the present invention is not limited to this. In the present invention, the image processor may alternatively be configured not to perform control to display the figure along the shape of the balloon as the expanded portion in the contrast image.

While the processing operations of the image processor 7c are described using a flowchart in a flow-driven manner in which the processing operations are performed in order along a processing flow for the convenience of illustration in the aforementioned embodiment, the present invention is not limited to this. In the present invention, the processing operations of the image processor may alternatively be performed in an event-driven manner in which the processing operations are performed on an event basis. In this case, the processing operations may be performed in a complete event-driven manner or in a combination of an event-driven manner and a flow-driven manner.

While the processed image P1 showing the expanded portion E in which the balloon 81 is expanded is created for the treatment of the region to be treated by expansion of the balloon 81 in the aforementioned embodiment, the present invention is not limited to this. The present invention can also be applied to treatment in which a device such as a stent is deployed in a region to be treated by expansion of a balloon. Generally, it is difficult to visually recognize a device such as a stent in a radiation image, and special processing such as processing for highlighting the device such as a stent is required for visual recognition. However, the present invention is applied such that a processed image showing a region in which a device such as a stent is deployed can be easily created, and thus an operator can easily visually recognize the region in which the device such as a stent is deployed in a radiation image.

What is claimed is:

1. A radiographic imaging apparatus comprising:
   an image generator configured to generate a plurality of radiation images based on detection signals of radiation transmitted through a subject;
   an image processor configured to perform image processing on the plurality of radiation images generated by the image generator;
   a storage; and
   a display configured to display a processed image that has been subjected to the image processing in the image processor,
   wherein the image processor is configured to:
   acquire an expanded portion of a balloon in a first radiation image among the plurality of radiation images,
   store the expanded portion of the balloon acquired in the first radiation image in the storage,
   generate the processed image to add information of the expanded portion of the balloon in the first radiation image stored in the storage, to a second radiation image among the plurality of radiation images, and
   determine if a position of the balloon in the processed image is different than the expanded portion of the balloon in the first radiation image.

2. The radiographic imaging apparatus according to claim 1, wherein the image processor is configured to perform control to acquire the expanded portion of the balloon based on an expansion recognition image in which expansion of the balloon introduced into the subject is recognized among the plurality of radiation images generated by the image generator.

3. The radiographic imaging apparatus according to claim 2, wherein the image processor is configured to perform control to acquire the expansion recognition image based on a change in a pixel value of a portion of the first radiation image showing the balloon and acquired based on a position of a balloon marker in the first radiation image.

4. The radiographic imaging apparatus according to claim 1, wherein the image processor is configured to perform control to create the processed image by superimposing a figure along a shape of the balloon on the expanded portion of the balloon in the first radiation image.

5. The radiographic imaging apparatus according to claim 1, wherein the image processor is configured to perform control to store the expanded portion of the balloon and create the processed image by showing the expanded portion of the balloon previously stored in the first radiation image when the balloon is expanded a plurality of times.

6. The radiographic imaging apparatus according to claim 1, wherein the image processor is configured to perform control to create an expanded-portion confirmation image by showing the expanded portion of the balloon in a contrast image of the subject captured with contrast medium and generated prior to an expansion recognition image in which expansion of the balloon introduced into the subject is recognized among the plurality of radiation images generated by the image generator.

7. The radiographic imaging apparatus according to claim 1, wherein the image processor is configured to perform control to correct the expanded portion of the balloon shown in the processed image based on detection of a displacement due to body movement of the subject or periodic movement of an object in the subject based on a comparison between a position of a feature point in an expansion recognition image in which expansion of the balloon introduced into the subject is recognized among the plurality of radiation images generated by the image generator and a position of a feature point in the first radiation image corresponding to the feature point in the expansion recognition image.

8. The radiographic imaging apparatus according to claim 1, wherein the image processor is configured to perform control to store the processed image created by showing the expanded portion in an expansion recognition image in which expansion of the balloon introduced into the subject is recognized among the plurality of radiation images generated by the image generator upon termination of acquisition of the radiation image of the subject when recognizing the expansion of the balloon introduced into the subject.

9. The radiographic imaging apparatus according to claim 1, wherein the image processor is configured to perform control to acquire an expansion duration time during which the balloon is expanded based on acquisition of an expansion recognition image in which expansion of the balloon introduced into the subject is recognized among the plurality of radiation images generated by the image generator and acquisition of a contraction recognition image, which is a radiation image in which contraction of the balloon introduced into the subject is recognized, after the acquisition of the expansion recognition image, and store the expansion duration time in association with the expansion recognition image.

10. The radiographic imaging apparatus according to claim 9, wherein the image processor is configured to perform control to create the processed image showing supplementary information including the expansion duration time in addition to the expanded portion.

11. A radiographic imaging apparatus comprising:
an image generator configured to generate a plurality of radiation images based on detection signals of radiation transmitted through a subject;
an image processor configured to perform image processing on the plurality of radiation images generated by the image generator;
a storage; and
a display configured to display a processed image that has been subjected to the image processing in the image processor,
wherein the image processor is further configured to:
  acquire an expansion recognition image based on a change in a pixel value of a portion of the radiation image showing a balloon and acquired based on positions of balloon markers in the plurality of radiation images,
  acquire an expanded portion of the balloon in a first radiation image among the plurality of radiation images based on the expansion recognition image,
  store the expanded portion of the balloon acquired in the first radiation image in the storage,
  generate the processed image to add information of the expanded portion of the balloon in the first radiation image stored in the storage, to a second radiation image among the plurality of radiation images, and
  determine if a position of the balloon in the processed image is different than the expanded portion of the balloon in the first radiation image.

12. The radiographic imaging apparatus according to claim 11, wherein the image processor is further configured to perform control to store the expanded portion of the balloon and create the processed image by showing the expanded portion of the balloon previously stored in the first radiation image when the balloon is expanded a plurality of times.

13. The radiographic imaging apparatus according to claim 11, wherein the image processor is further configured to perform control to create an expanded-portion confirmation image by showing the expanded portion of the balloon in a contrast image of the subject captured with contrast medium and generated prior to the expansion recognition image in which expansion of the balloon introduced into the subject is recognized among the plurality of radiation images generated by the image generator.

14. A radiographic imaging apparatus comprising:
an image generator configured to generate a radiation image based on detection signals of radiation transmitted through a subject;
an image processor configured to perform image processing on the radiation image generated by the image generator; and
a display configured to display a processed image that has been subjected to the image processing in the image processor,
wherein the image processor is configured to perform control to create the processed image that adds an information showing a post-treatment expanded portion in which a balloon introduced into the subject is expanded with respect to the radiation image, and
wherein the image processor is configured to perform control to acquire an expansion duration time during which the balloon is expanded based on acquisition of an expansion recognition image in which expansion of the balloon introduced into the subject is recognized among radiation images generated by the image generator and acquisition of a contraction recognition image, which is the radiation image in which contraction of the balloon introduced into the subject is recognized, after the acquisition of the expansion recognition image, and store the expansion duration time in association with the expansion recognition image.

15. The radiographic imaging apparatus according to claim 9, wherein the image processor is configured to perform control to create the processed image showing supplementary information including the expansion duration time in addition to the expanded portion.

* * * * *